United States Patent
Murakami et al.

(10) Patent No.: US 7,485,769 B2
(45) Date of Patent: Feb. 3, 2009

(54) TRANSGENIC MAMMALS

(75) Inventors: Hiroshi Murakami, Tsukuba (JP); Tatsuya Fujimura, Tsukuba (JP); Yoichi Takahagi, Tsukuba (JP); Koji Toyomura, Tsukuba (JP); Tamotsu Shigehisa, Tsukuba (JP)

(73) Assignee: Nippon Meat Packers, Inc., Osaka-shi (JP)

( * ) Notice: Subject to any disclaimer, the term of this patent is extended or adjusted under 35 U.S.C. 154(b) by 154 days.

(21) Appl. No.: 10/362,429

(22) PCT Filed: Aug. 27, 2001

(86) PCT No.: PCT/JP01/07331

§ 371 (c)(1),
(2), (4) Date: Feb. 25, 2003

(87) PCT Pub. No.: WO02/15681

PCT Pub. Date: Feb. 28, 2002

(65) Prior Publication Data

US 2004/0073963 A1    Apr. 15, 2004

(30) Foreign Application Priority Data

Aug. 25, 2000 (JP) .............................. 2000-256541

(51) Int. Cl.
  *A01K 67/027*  (2006.01)
  *C12N 15/00*  (2006.01)
(52) U.S. Cl. .............................. 800/17; 800/14; 800/21; 800/22; 800/25
(58) Field of Classification Search .................. 800/14, 800/17, 18, 21, 22, 25
See application file for complete search history.

(56) References Cited

U.S. PATENT DOCUMENTS 6,166,288 A * 12/2000 Diamond et al. .............. 800/17

FOREIGN PATENT DOCUMENTS

| JP | 11-239430 | 9/1999 |
| WO | WO 97/12035 A2 | 4/1997 |
| WO | WO 97/44449 A1 | 11/1997 |

OTHER PUBLICATIONS

Kappel et al., 1992, Current Opinion in Biotechnology, vol. 3, p. 548-553.*
Sigmund, C., Jun. 2000, Arterioscler. Thromb. Vasc. Biol., p. 1425-1429.*
Houdebine, L-M., 2002, Journal of Biotechnology, vol. 98, p. 145-160.*
Ihara et al., 1998, Proc. Natl. Acad. Sci. USA, vol. 95, pp. 2526-2530.*
Wall, R. J., 1996, Theriogenology, vol. 45, p. 57-68.*
Mercier et al., 1997, "The modification of milk protein composition through transgenesis: progress and problems," In: Transgenic Animals: Generation and use, Ed. Houdebine LM, Harwood Academic Publishers, The Netherlands pp. 473-482.*
Koo et al., 2001, Molecular reproduction and Development, vol. 58, p. 15-21.*
Niemann et al., 2001, Theriogenology, vol. 56, p. 1291-1304.*
Tanemura, M., et al. Transplantation Proceedings, vol. 29, No. 1/2, pp. 895-896, 1997.
Miyagawa, S., et al. J. Biochem., vol. 126, No. 6, pp. 1067-1073, 1999.
Miyagawa, S., et al. Biochemical and Biophysical Research Communications, vol. 264, No. 3, pp. 611-614, 1999.
Ihara, Y., et al. J. Biochem., vol. 113, No. 6, pp. 692-698, 1998.
Masaru Koma, et al., "Reduction of the Major Xenoantigen on Glycosphingolipids of Swine Endothelial Cells by Various Glycosyltransferases", Glycobiology, vol. 10, No. 7, Jul. 2000, pp. 745-751, XP002344601.
Tanemura et al., Biochemical and Biophysical Research Communications, vol. 235, p. 359-364 (1997).
Ihara, Y., et al. J. Biochem., vol. 113, No. 6, pp. 696-698, (1993).
Souichi et al., Cell Engineering vol. 19 No. 6, p. 836-843, (2000).

* cited by examiner

*Primary Examiner*—Shin-Lin Chen
(74) *Attorney, Agent, or Firm*—Birch, Stewart, Kolasch & Birch, LLP

(57) ABSTRACT

This invention provides a nonhuman transgenic mammal carrying transgene comprising the regulatory genes capable of functioning in the hyperacute rejection-occurring local cells and gene encoding human N-acetylglucosaminyltransferase III (GnT-III), or a nonhuman transgenic mammal carrying transgene comprising the regulatory genes and genes encoding GnT-III and the human complement inhibitor. Because of reduced α-Gal antigens in the hyperacute rejection-occurring local cells or because of both reduced α-Gal antigens and expression of the human complement inhibitor, the transgenic mammal of this invention can effectively inhibit the hyperacute rejection caused by discordant xenotransplantation. Consequently, this invention provides the transgenic mammal suitable for organ transplantation.

4 Claims, 5 Drawing Sheets

SEQUENCE LISTING

```
<160> NUMBER OF SEQ ID NOS: 5

<210> SEQ ID NO 1
<211> LENGTH: 39
<212> TYPE: DNA
<213> ORGANISM: Artificial Sequence
<220> FEATURE:
<223> OTHER INFORMATION: Promoter region of pMCP gene.

<400> SEQUENCE: 1
tcctcgagct gccccggctg ctgctgctgg tgctgttgt                    39

<210> SEQ ID NO 2
<211> LENGTH: 30
<212> TYPE: DNA
<213> ORGANISM: Artificial Sequence
<220> FEATURE:
<223> OTHER INFORMATION: Primer used to amplify first intron of DAF.

<400> SEQUENCE: 2
tcaagcttct gggggaaggc cacagtcacc                              30

<210> SEQ ID NO 3
<211> LENGTH: 22
<212> TYPE: DNA
<213> ORGANISM: Artificial Sequence
<220> FEATURE:
<223> OTHER INFORMATION: GnT-III cDNA sense primer directed to DNA from
      pig.

<400> SEQUENCE: 3
```

```
ggtggacgcc tttgtggtgt gc                                              22

<210> SEQ ID NO 4
<211> LENGTH: 22
<212> TYPE: DNA
<213> ORGANISM: Artificial Sequence
<220> FEATURE:
<223> OTHER INFORMATION: GnT-III cDNA anti-sense primer directed to DNA
      from pig.

<400> SEQUENCE: 4
gccggtgcgg ttctcatact gt                                              22

<210> SEQ ID NO 5
<211> LENGTH: 36
<212> TYPE: DNA
<213> ORGANISM: Artificial Sequence
<220> FEATURE:
<223> OTHER INFORMATION: Primer directed to first intron of DAF.

<400> SEQUENCE: 5
tcctcgagct gccccggctg ctgctggtgc tgttgt                               36
```

TRANSGENIC MAMMALS

This application is the national phase under 35 U.S.C. § 371 of PCT International Application No. PCT/JP01/07331 which has an International filing date of Aug. 27, 2001, which designated the United States of America.

TECHNICAL FIELD

This invention provides a transgenic mammal, particularly, a nonhuman transgenic mammal carrying a gene encoding human N-acetylglucosaminyltransferase III capable of reducing the α-galactosyl antigen. Moreover, it provides a nonhuman transgenic mammal carrying genes encoding both human N-acetylglucosaminyltransferase III capable of reducing the α-galactosyl antigen and a human complement inhibitor.

BACKGROUND OF THE INVENTION

Organ transplantation is a very valuable and radical therapy. Such organs as the kidney, liver and heart have been transplanted to treat some organ failure. Transplantation can be classified into allotransplantation (transplantation between a donor and a recipient of the same species) and xenotransplantation (that between those of different species). Such transplantation has both advantages and disadvantages. Allotransplantation is superior to the xenotransplantation because of less rejection, but the former is inferior to the latter because of shortage of human donors. Recently, animal-to-man organ transplantation (xenotransplantation) has been studied mainly in European countries and the United States. Apes may be desirable donors because of close relation to human beings, but the use of their organs may be infeasible because of the shortage of these animals and their high intelligence. However, farm animals, particularly pigs, have advantages of their organ sizes and shapes similar to those of man, abundant supply due to mass rearing and established basic technology. Consequently, the pig-to-man organ transplantation has mainly been studied. Xenotransplantation between closer species (e.g., baboon-to-man) and that between more distant species (e.g., pig-to-man) are called concordant and discordant xenotransplantation, respectively.

In pig-to-man discordant xenotransplantation, the xenograft will be rejected within minutes. Such a phenomenon is called hyperacute rejection, which is initiated by the reaction between natural antibodies in the human serum and the xenoantigens in the porcine xenografts (organs, tissues, cells, etc.), resulting in complement-dependent cell injury (complement reaction).

Gal α 1,3Gal (referred to as α-Gal antigen hereafter) at non-reducing terminals of sugar chains (sugar protein and sugar lipid) on the porcine cells has been regarded as one of the significant xenoantigens. The α-Gal antigen is synthesized upon addition of α-1,3-galactose to N-acetyl-lactosamine by α-1,3-galactosyltransferase (hereafter referred to as α-1,3GT) (FIG. 1).

Human tissue do not expresse α-Gal antigen. Of mammals, Old World monkeys (inhabiting in Asia and Africa), anthropoids (the chimpanzee, gorilla and orangutan) and man, taxonomically stemmed out 20-30 million years ago, are carrying the frame-shifted α-1,3GT pseudogene (J. Biol. Chem., 265: 7055-7061 (1990)) but producing the natural antibodies against the α-Gal antigens. It has been reported that anti-α-Gal antibody comprises as much as 1% of human IgG (Blood, 82: 2485-2493 (1993)).

Even if hyperacute rejection is overcome, such graft failure as endothelial swelling, ischemia and thrombosis will occur. Histologically, coagulation of platelets, deposit of fibrin, activation of endothelia and invasion of activated macrophages and NK cells will occur. Such a phenomenon is called acute vascular rejection (AVR) or delayed xenograft rejection (DXR). Xenoreactive antigens, complement, macrophages, NK cells, neutrophils and platelets may be the factors implicated in initiation of AVR.

The method preventing hyperacute rejection includes those applicable to the recipients and those applicable to the donors. An example of the former is adsorption of the natural antibodies onto immunologically-prepared columns, and those of the latter are expression of the recipients' complement inhibitors and reduction of the α-Gal antigens. Because the natural antibodies can hardly be removed from the recipients, the treatments of the donors are generally adopted. Because the xenoantigens may cause AVR, reduction in the α-Gal antigens may be effective on retarding or preventing AVR.

The methods to reduce the donors' α-Gal antigens are as follows:

(1) Reduction of α-Gal antigen by digestion of α-galactosyl bond at a sugar-chain terminal with α-galactosidase Although α-galactosidase from coffee beans is known, the enzyme failed to physiologically digest the α-Gal antigen because of its optimum pH ranging between 6 and 6.5.

(2) knock out (KO) of α-1,3GT gene responsible for α-Gal antigen production

Although α-1,3GT gene-KO mice were developed (Transplantation, 61: 13-19 (1996)), they suffered from cataract. Since pigs are expressing more α-Gal antigens than mice, α-1,3GT gene-KO pigs may cause severer adverse effects.

Furthermore, KO-pig development itself has been infeasible, because no porcine embryonic stem (EC) cell has been established.

(3) competitive prevention of α-1,3GT gene by introducing genes of other sugar transferases sharing the same substrate (N-acetyllactosamine)

α-Fucosyltransferase (α-1,2FT) gene was introduced to convert galactose of the α-Gal antigens (Gal α 1,3Gal) synthesized by α-1,3GT to fucose or an H blood-type substance (WO095/34202A1). Such methods may reduce the α-Gal antigens, because galactose at the non-reducing sugar-chain terminals is replaced with other sugars. However, the overall reduction of the α-Gal antigens is negligible, unless expression of the introduced gene exceeds that of the endogenous α-1,3GT gene. Moreover, such methods can not reduce the number of sugar chains or their branches themselves in contrast with N-acetylglucosaminyltransferase III described later.

(4) Forced expression of N-acetylglucosaminyltransferase III (β-D-mannoside β-1,4 N-acetylglucosaminyltransferase III, EC 2.4.1.144: referred to as GnT-III in the following) to prevent N-linked sugar chain from branching Forced expression of GnT-III results in prevention of sugar-chain branching and α-Gal antigen production. The mechanisms of sugar-chain branching and its prevention by GnT-III are illustrated in FIG. 2.

Generally, the sugar chains can be classified into N-, O- and lipid-linked ones. Each sugar chain has a core structure, from which the sugar chain extends to its terminal. Such extension will end, if α-1,3 galactose is added. Similarly, α-1,2FT will stop the sugar-chain extension from a core structure of N-acetyllactosamine. Consequently, such transferases are antagonistic to α-1,3GT (see FIG. 1). However, GnT-III relates to formation of the core structure of N-linked sugar chains like other N-acetylglucosaminyl (GlcNAc)transferases and is not antagonistic to other sugar transferases.

N-linked sugar chains can be classified into two-, three- and four-branched ones. As FIG. 2 shows, GnT-IV and GnT-V catalyze introduction of a sugar branch to a precursor two-branched sugar chain, resulting in three- and four-branched ones. GnT-I and GnT-II catalyze introduction of a branch to a precursor of a core N-linked sugar chain, resulting in two-branched one. If GlcNAc is added to β-mannose (β-Man) of the core structure by GnT-III, no sugar chain can extend at all. Such GlcNAc is, therefore, distinguished from other GlcNAc and called bisecting GlcNAc. If bisecting GlcNAc is added to a two-branched sugar chain, neither GnT-IV nor GnT-V will use it as their substrate nor synthesize three- or four-branched sugar chains. Arrows with squares in FIG. 2 indicate such inhibition of the enzymatic reactions.

The two-branched sugar chain with bisecting GlcNAc inhibits β-galactosyl and α-galactosyl reactions as well as α-Gal antigen synthesis (Glycobiol., 6: 691-694 (1996)). In summary, forced expression of GnT-III reduces the sugar-chain branching and the α-Gal antigen production of not only each sugar chain but also the entire cell.

As for GnT-III-introduced transgenic animals, transgenic mice were generated by a transgene comprising rat GnT-III cDNA, β-actin promoter and cytomegalovirus enhancer (Transplant. Proc., 29: 895-896 (1997)). Their hearts, lungs and livers expressed more GnT-III and less α-Gal antigens than did those in normal mice. The normal mice, however, expressed much GnT-III (3,400 p mol/h/mg protein) in their kidneys. Although the transgenic mice expressed more GnT-III (4,800 p mol/h/mg protein) in their kidneys, they failed to reduce the α-Gal antigens in their kidneys. Namely, the transgenic mice carrying the rat GnT-III gene failed to reduce the α-Gal antigens in their organs, especially their kidneys.

No GnT-III-introduced transgenic pig has ever been generated. Viviparous mammals except marsupials and anthropoids express the α-Gal antigens on their cell membranes. Particularly, porcine organs express much α-Gal antigens. For example, porcine kidneys express 500- to 1,000-times more α-Gal antigens than do mouse kidneys. The α-Gal antigens may be indispensable for development and survival of pigs. They may mask the bacterial receptors and prevent infection (Cell Engineering, 19: 830-834 (2000)). As described later, no normal pig organ such as the kidney expresses GnT-III at all. It has been unknown whether or not artificial expression of GnT-III on porcine organs, tissues or cells affects porcine development and survival, and whether the artificial expression of GnT-III reduces the α-Gal antigens. Of promoters used to construct transgenes, it is known that some can not necessarily induce expression of objective structure genes in pigs, even if they effectively work in mice (e.g., Theriogenol. 51: 422 (1999)). Consequently, no gene promoter effectively inducing expression of the human GnT-III in pigs has been known.

Particularly, the following have been unknown, (1) whether liveborn transgenic piglings can be generated from embryos injected with GnT-III gene (especially, the human GnT-III gene), (2) even if the transgenic pigs carrying the human GnT-III gene are generated, whether their organs can express GnT-III and reduce the α-Gal antigens, (3) whether liveborn transgenic pigs carrying both the GnT-III gene and one or more transgenes other than GnT-III in their individual bodies can be generated, (4) whether their organs can express GnT-III, reduce the α-Gal antigens and express one or more transgenes other than GnT-III gene, and (5) if one or more transgenes expressing along with the sugar-chain remodeling GnT-III gene is (are) a sugar protein(s) (e.g., human DAF), whether expression of GnT-III will injure expression of such sugar protein(s) (e.g., the human DAF).

Since hyperacute rejection takes place in local cells (e.g., vascular endothelial cells), such transgenic mammals with reduced N-linked sugar-chain branches and reduced α-Gal antigens in local cells have been desired.

Since complement-dependent cell injury (complement reaction) initiates hyperacute rejection, generation of transgenic mammals expressing complement inhibitor (human complement inhibitor in case of human recipients) and less α-Gal antigens have been desired to suppress the complement reaction of the transplantation recipient.

DISCLOSURE OF THE INVENTION

The present invention was originated to solve the above-mentioned problems. First, this invention provides a nonhuman transgenic mammal (especially transgenic pig) with reduced N-linked sugar-chain branches and reduced α-Gal antigens in the hyperacute rejection-occurring local cells.

Second, this invention provides a nonhuman transgenic mammal (especially the transgenic pig) with reduced N-linked sugar-chain branches, reduced α-Gal antigens and the human complement inhibitor in the hyperacute rejection-occurring local cells. Moreover, this invention provides also a method of generating such a nonhuman transgenic mammal.

THE BEST MODE FOR APPLYING THE INVENTION

Figure 1:
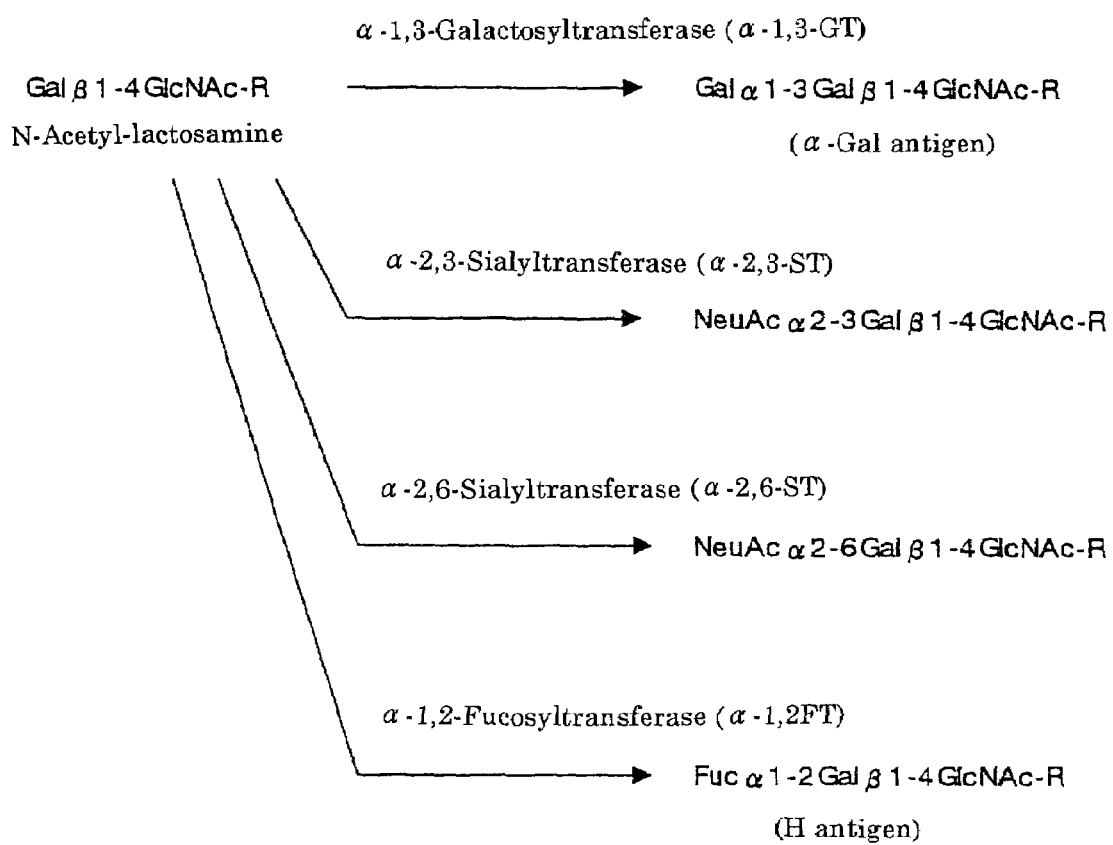
FIG. 1 illustrates the mechanisms of α-Gal antigen formation and prevention of its formation.
Figure 2:
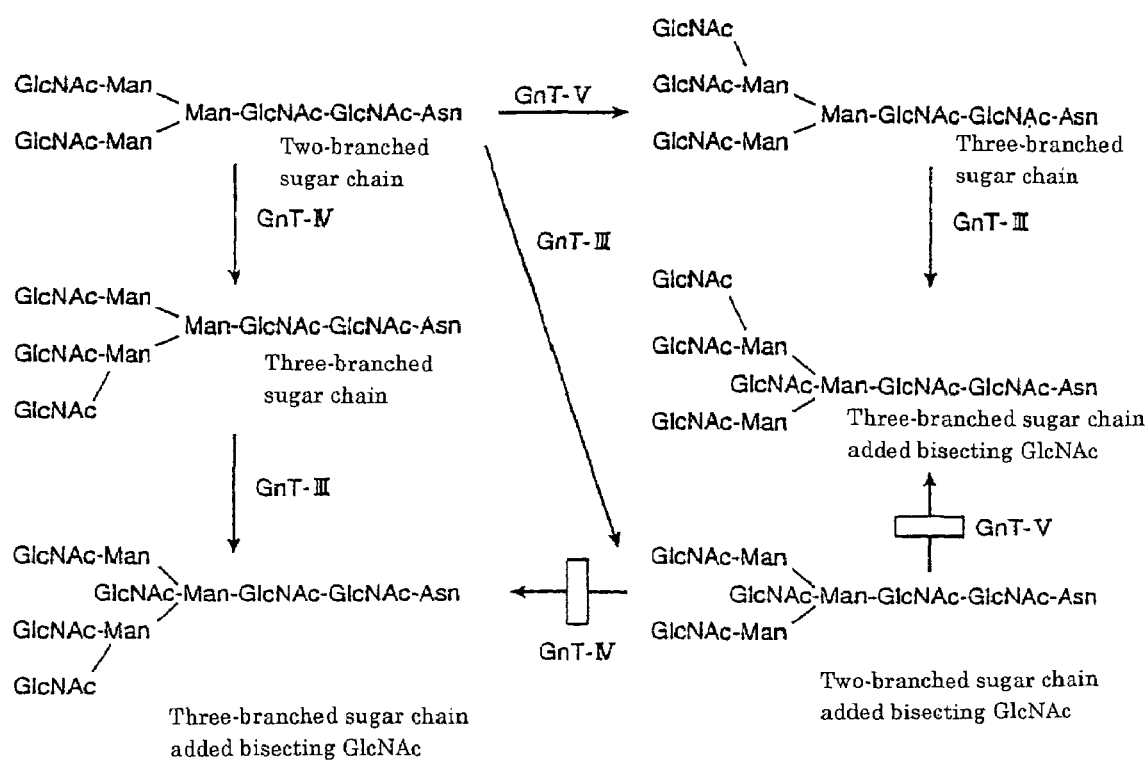
FIG. 2 illustrates how the sugar chains branch and how GnT-III prevents the sugar chains from branching.

To solve the above-mentioned problems, the present invention provides a nonhuman transgenic mammal carrying the transgene comprising regulatory gene functioning in the hyperacute rejection-occurring local cells and the human N-acetylglucosaminyltransferase III (GnT-III) gene (referred to as the first invention in the following for convenience). Such a transgenic mammal is characterized by possessing reduced N-linked sugar-chain branches and reduced α-Gal antigens.

The present invention provides a nonhuman transgenic mammal carrying transgene comprising the regulatory gene functioning in the hyperacute rejection-occurring local cells, GnT-III gene and the human complement-inhibitor gene (referred to as the second invention in the following for convenience). Such a transgenic mammal is characterized by possessing reduced N-linked sugar-chain branches and reduced α-Gal antigens and expressing the human complement inhibitor.

Furthermore, the present invention provides the method of generating a nonhuman transgenic mammal comprising generation of transgenic mammals expressing GnT-III and that expressing the human complement inhibitor followed by crossbreeding both of them.

As mentioned above, the first invention provides the nonhuman transgenic mammal carrying the GnT-III gene and expressing reduced N-linked sugar-chain branches and reduced α-Gal antigens in the hyperacute rejection-occurring local cells.

The second invention provides the nonhuman transgenic mammal carrying the transgene comprising regulatory gene functioning in the hyperacute rejection-occurring local cells and genes of GnT-III and the human complement inhibitor, or those expressing reduced N-linked sugar-chain branches, reduced α-Gal antigens and the human complement inhibitor. The invention provides the method of generating such a nonhuman transgenic mammal.

The species of the mammal of this invention is not restricted, as far as it is nonhuman. Farm animals and experimental animals are examples. More particularly, such animals as the pig, bovine, equine, ovine, goat, dog, rabbit, mouse, rat, guinea pig, and hamster are examples. As mentioned above, the pig is desirable in organ transplantation to man.

This invention uses the human GnT-III gene to reduce both N-linked sugar-chain branches and the α-Gal antigens. The gene is well known and can be prepared by PCR amplification with proper primers from the human GnT-III inserted vector (J. Biochem. 113: 692-698 (1993)).

N-linked sugar chains, of which reducing terminals are linked to the amide terminals of asparagine of peptide by N-glycosyl bond, are distinguished from O-linked sugar chains, of which non-reducing terminals are linked to the hydroxyl terminals of serine or threonine of peptide chains. Since principal targets of the human natural antibody are N-linked sugar chains in the porcine endothelial cells (Transplantation, 50: 817-822 (1990)), this invention effectively prevents hyperacute rejection due to reduced α-Gal antigens by the GnT-III expression.

As the complement inhibitors of this invention, genes of such known human complement inhibitors as DAF (CD55), CD59 and MCP (CD46) can be used. In case of MCP, gene encoding a protein lacking the MCP's short consensus repeat (SCR) 1, functioning as a measles virus receptor, can be used. Similarly, gene encoding a modified protein lacking SCR1, transmembrane and intracellular domains of MCP but possessing a signal peptide to express glycosylphosphatigyl inositol (GPI) anchor can be used (Japanese Patent Application No.2000-131862). As far as the complement inhibitory functions are available, such modified complement inhibitors as C1 inhibitor, C4-binding protein, H and I factors, which are originally soluble and circulating complement inhibitors, can be used in addition to such membrane-linked complement inhibitors as DAF (CD55), CD59 and MCP (CD46).

As below-described examples show, expression of reduced N-linked sugar-chain branches and reduced α-Gal antigens and that of the human complement inhibitor in the hyperacute rejection-occurring local cells synergistically reduce the complement-dependent cell injuries.

To express genes encoding GnT-III and/or the human complement inhibitors in the hyperacute rejection-occurring local cells, regulatory genes capable of functioning on the local cells should be used. As such regulatory genes, those of genes encoding proteins functioning in the hyperacute rejection-occurring local cells are preferably used. The regulatory genes are DNA sequences regulating increment and/or decrement of transcriptional rates of gene. Examples of the regulatory genes are promoter, enhancer, upstream-activating sequence, silencer, upstream-inhibiting sequence, attenuator, etc. but not restricted to them.

Such a promoter is not restricted, as far as it can make genes of the GnT-III and/or the human complement inhibitor express in the hyperacute rejection-occurring local cells.

Examples are promoters of β-actin, albumin, insulin, elongation factor, and such endothelium-relating protein as endothelin and thrombomodulin. To make the donors express the target proteins, the promoters from donor species are preferably used. If a transgenic animal is the pig, the promoter of porcine complement inhibitor (pMCP) is more preferably used (Japanese Patent Publication KOKAI No. 66584/1998). The example described in the following shows that βactin promoter can effectively make GnT-III express on the porcine endothelial cells.

The above-described enhancer is not restricted, as far as it can make genes of the GnT-III and/or the human complement inhibitor express in the hyperacute rejection-occurring local cells. Examples are the cytomegalovirus enhancer and the first intron of human DAF gene.

The transgenic animal of this invention can conventionally be generated with a transgene satisfying the embodiment of this invention.

In case of the first invention, a transgene comprising GnT-III gene and a regulatory gene functioning in the hyperacute rejection-occurring local cells are constructed and subjected to generation of the transgenic mammal.

The above-described transgene can conventionally be prepared. For example, a transgene comprising pMCP promoter, the first intron of human DAF and GnT-III gene is prepared as follows:

First, a part of an appropriate vector (e.g., pGL-3 basic vector, pBluescript, etc.) is clipped out with a restriction enzyme(s), and the end of the vector side is truncated.

Next, a promoter region of pMCP gene (Japanese Patent Publication KOKAI No. 65887/1997)is clipped, deleted to obtain a 0.9-kb promoter gene (the sequence from the 4,498th to the 5,397th bases of SEQ ID NO:1 of Japanese Patent Publication KOKAI No. 6887/1997), truncated both ends and inserted to the above-described vector.

The first intron area of DAF gene is amplified by PCR with appropriate primers and human genomic gene as a template and inserted into the downstream locus of the pMCP promoter of the above-described vector.

Poly A signal-added GnT-III cDNA (J. Biochem. 113: 692-698 (1993)) is inserted into the downstream locus of the first intron of DAF.

A transgene comprising pMCP promoter, the first intron of DAF and GnT-III gene can be prepared by properly clipping the vector thus prepared. To prepare a transgene comprising genes of GnT-III and DAF, the latter is inserted into an upstream or downstream locus of the former. The methods in the above-described processes are known and can be applied by those skilled in the art.

Transgenic mammals can conventionally be generated by microinjecting the above-described transgenes into pronuclei of mammals' fertilized eggs (those at the pronucleus phase), implanting the eggs after additional incubation or directly to the uteri or oviducts of female recipient mammals synchronized to pseudopregnancy, and obtaining the youngs. If the pronuclei are difficult to be recognized because of the presence of many fatty granules in the eggs, they may conventionally be centrifuged previously. To confirm that the generated youngs are transgenic, below-described dot-blotting, PCR, immunohistological examination, or complement-inhibition assay can be carried out.

The transgenic mammals can be generated by applying the nuclear-transfer technique more specifically, by one of the following methods:

(1) Somatic cells (e.g., mammary gland cell, fibroblast, granulosa cell and cumulus cell) in case of animal species whose embryonic stem (ES) cell has not been established, and ES or somatic cells in case of ES cell-established species (e.g., mouce) are transformed by such conventional methods as electroporation or lipofection with the transgenes described above or constructed to additionally carry antibiotic-resistant genes as markers;

(2) Oocytes of animals, of which species are identical to the transformed cells, are collected and enucleated;

(3) The youngs are obtained by fusing the transformed cells of (1) with the enucleated oocytes of (2) or injecting karyoplasts of (1) into the enucleated oocytes of (2), and then activating, incubating and implanting the reconstructed embryos in the uteri or oviducts of female recipient mammals synchronized to pseudopregnancy.

Furthermore, preparation of each of transgenic mammals expressing GnT-III and the human complement inhibitor following crossbreeding of both sexually matured animals can generate transgenic mammals expressing both GnT-III and the human complement inhibitor.

Transgenic mammals carrying the GnT-III gene and those carrying both genes of GnT-III and the human complement inhibitor thus-generated are characterized by reduced N-linked sugar-chain branches and reduced α-Gal antigens in the hyperacute rejection-occurring local cells.

The state of reduced α-Gal antigens is defined as that the amount of the α-Gal antigens of N-linked sugar chains expressed in the cells of the transgenic mammals is less than that of non-modified or wild animals by at least over 30%, desirably over 50%, more desirably over 60% and most desirably over 70%.

Examples of organs of the transgenic mammals of this invention expressing GnT-III and those expressing both GnT-III and the human complement inhibitor are the liver, lung, kidney, heart, pancreas, digestive organs as intestines, and eye, but they are not restricted to these. Examples of tissues of transgenic mammals of this invention are the brain, skin, subcutaneous tissue, epithelial tissue, bone and muscle, but they are not restricted to these. Examples of cells of transgenic mammals of this invention are the endothelial cells located in the above-described organs or tissues, hepatocyte, pancreatic cell, nerve cell, nigrostriatal cell, zygote, oocyte and embryonic stem cell, but they are not restricted to these samples.

INDUSTRIAL APPLICABILITY

The transgenic mammal of the first invention of this invention effectively inhibit hyperactute rejection caused by discordant xenotransplantation because of reduced α-Gal antigens in the hyperacute rejection-occurring local cells. The transgenic mammals of the second invention of this invention more effectively inhibit the hyperactute rejection because of reduced α-Gal antigens and expression of the human complement inhibitor in the local cells.

If the organs (e.g., the heart, lung, liver, kidney, pancreas, etc.), their adjunctive tissues (e.g., the coronary artery, dura mater, etc.) or cells (e.g., Langerhans islet producing insulin, nigrostriatal cell producing dopamine, etc.) from the transgenic mammals of this invention are transplanted to human patients whose organs have been damaged, they will supplement or substitute the functions of the patients' organs.

If the cells from the organs of the transgenic mammals of this invention (e.g., cells from the liver, kidney, etc. Langerhans islets producing insulin, nigrostriatal cells producing dopamine) are cultured, put in an appropriate device, and connected with human patients ex vivo, it will supplement or substitute the functions of the damaged organs of the patients.

EXAMPLES

The present invention will specifically be explained in detail in Examples, but the scope of the invention is not restricted to these.

Example 1

Figure 3:
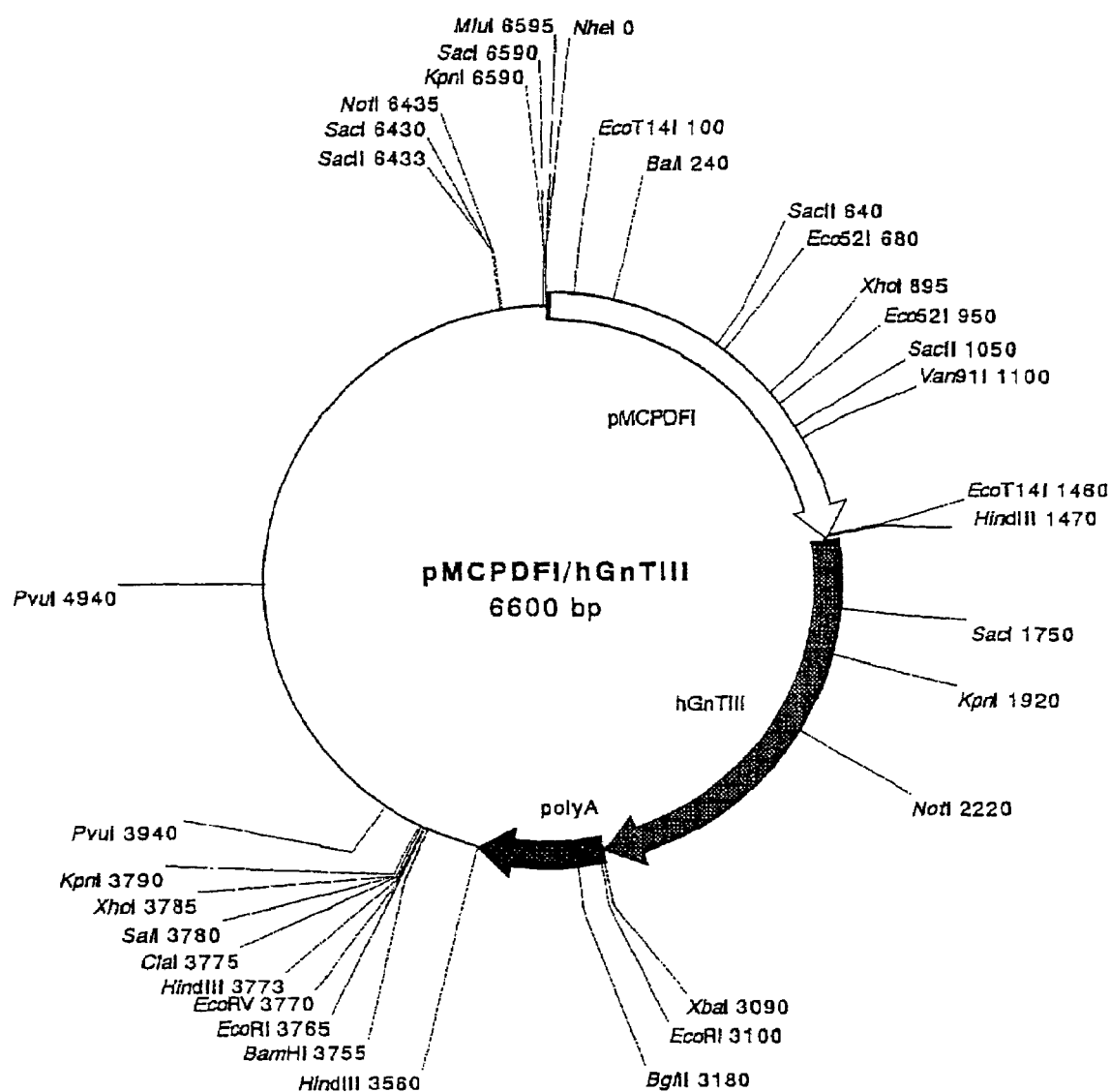
FIG. 3 illustrates the transgene structure of Example 1.

Transgenic Pigs Generated with a Transgene Comprising pMCP Promoter, the First Intron of DAF and cDNA of GnT-III (a) Preparation of the Transgene A transgene comprising pMCP promoter, the first intron of DA.F and cDNA of GnT-III was prepared and is shown in FIG. 3. The transgene was prepared in the following way:

(1) A 1.7-kb promoter region of pMCP (Japanese Patent Publication KOKAI No. 65887/1997) was clipped out at the BstEII and BamHi sites from a porcine genomic phage library, truncated with T4 DNA polymerase, and then inserted into the SmaI site of a pBluescript vector (Stratagene). The vector was clipped out at the BstXI and SpeI sites located at further upstream loci of the promoter and linearized, digested with a Kilo-Sequence deletion kit is (Takara) to obtain a deletion mutant possessing the 0.9-kb promoter gene (the sequence from the 4,498th to the 5,397th bases of SEQ. ID. No. 1 of Japanese Patent Application No. 142961/1997), truncated with T4 DNA polymerase and then inserted at the SmaI site of pGL-3 basic vector (Promega);

(2) The first intron of DAF was amplified with primers of

5'-TCCTCGAGCTGCCCCGGCTGCTGCTG-GTCGTGTTGT (SEQ ID NO:5) and

5'-TCAAGCTTCTGGGGAAGGCCACAGTCACC (SEQ ID NO:2) and the human genomic library as a template. A fragment with XhoI and HidIII sites was obtained and inserted to the XhoI and HidIII sites of the above-described vector;

(3) A poly A signal sequence was added to GnT-III cDNA (J. Biochem. 113: 692-698 (1993)) and inserted to the XhoI and HidIII sites of the above-described vector;

(4) A region containing pMCP promoter, the first intron of DAF and GnT-III was clipped out at the MluI site and dissolved in phosphate-buffered saline (PBS) at 4 μg/ml.

(b) Generation of Transgenic Pigs

Transgenic pigs were generated by the microinjection method with above-described transgene. The method to generate the transgenic pigs is outlined as follows (see Japanese Patent Publication KOKAI No. 239430/1999):

Fertilized eggs were collected from hybrid female pigs of Landrace, Large White and Duroc. After induction of ovulation of the donor pigs (by administration of either PMSG or FSH, and hCG) and artificial insemination with Duroc pig, the fertilized eggs (those at the prenucleus phase) were collected. After centrifugation (for 8 min at 12,000×g) of the prenucleus-phase eggs, the above-described transgene was injected into the prenuclei. The transgene-injected eggs were immediately implanted to the oviducts of the recipient pigs, and then piglings were obtained. The recipient pigs were those of which sexual cycles had been synchronized to the donor pigs by the above-described ovulation treatment or those from which fertilized eggs had been collected.

(c) Identification and Selection of Transgenic Pigs

Genomic DNA was extracted from the tails of the piglings obtained from the recipient pigs and subjected to identification and selection of transgenic pigs by either of the following two methods:
(1) The dot-blotting method: Genomic DNA (10 μg) from the piglings was placed on a piece of membrane and hybridized with gene comprising a part of biotin-labeled GnT-III cDNA. The transgenic pigs were identified by detecting the introduced transgene by an alkaline phosphatase-dependent chromogenic reaction (a DIG nucleic-acid detection kit, Boehlinger Manheim);
(2) PCR method: PCR was carried out (conditions; denaturation for 30 sec at 94° C. and annealing for 2 min and 30 sec at 68° C., 30 times) with genomic DNA from piglings as a template, 5'-GGTGGACGCCTTTGTGGTGTGC of (SEQ ID NO:3) of GnT-III cDNA as a sense primer and 5'-GCCGGTGCGGTTCTCATACTGT as (SEQ ID NO:4) an antisense primer. Amplified samples were electrophoresed in miniature gel (ethidium-bromide added) to identify the introduced transgene.

With the pigs identified as transgenic, their descendants were generated and selected by the above-described identification methods.

Example 2

Figure 4:
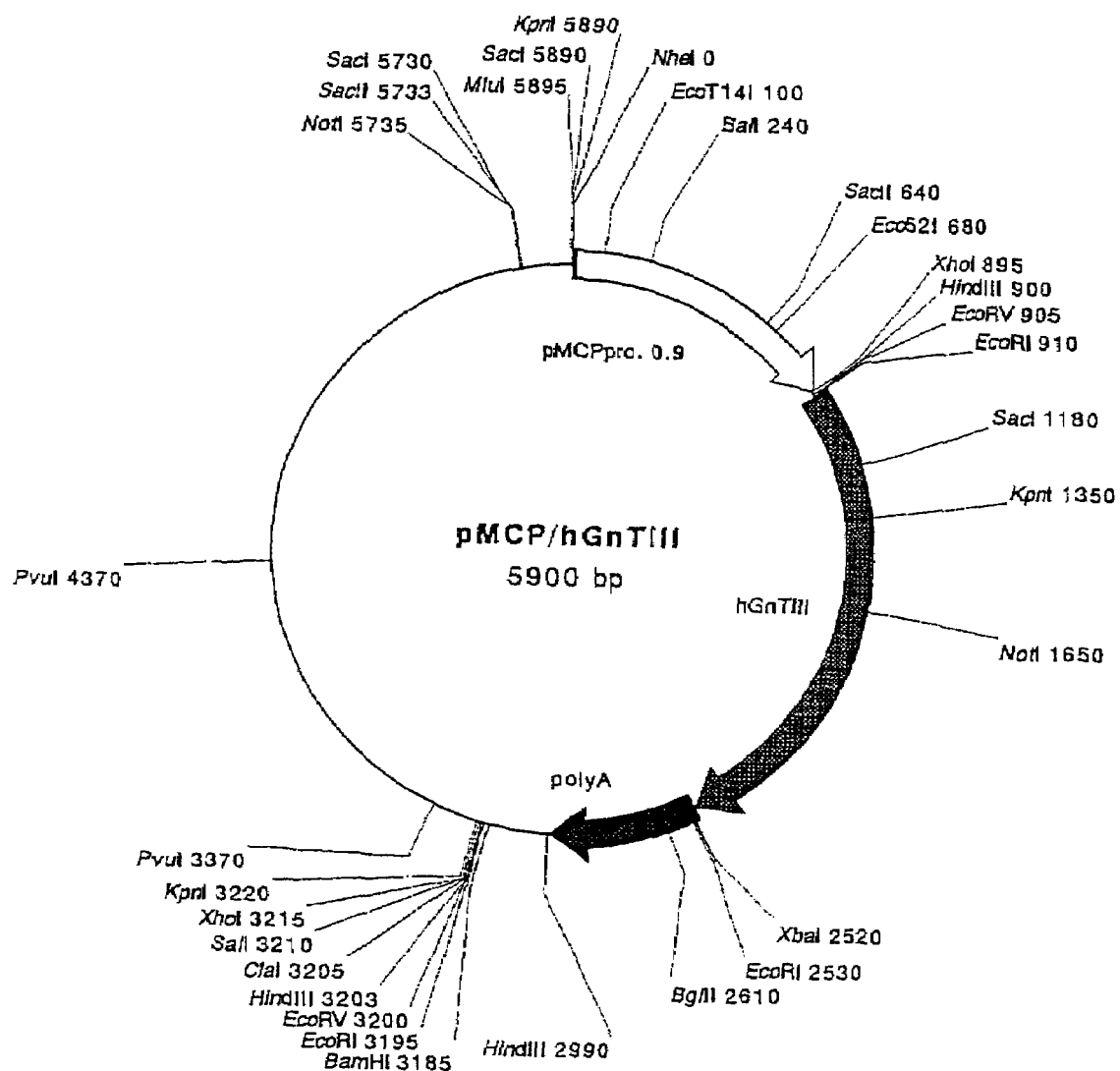
FIG. 4 illustrates the transgene structure of Example 2.

Transgenic Pigs Generated with a Transgene Comprising pMCP Promoter and cDNA of GnT-III A transgene comprising the pMCP promoter and cDNA of GnT-III was prepared. As shown in FIG. 4, it was identical to Example 1, except for lacking the first intron of DAF. Transgenic piglings were obtained. Consequently, it was confirmed that liveborn transgenic pigs could be generated from the embryos introduced with GnT-III gene (especially, the human GnT-III gene).

Example 3

Figure 5:
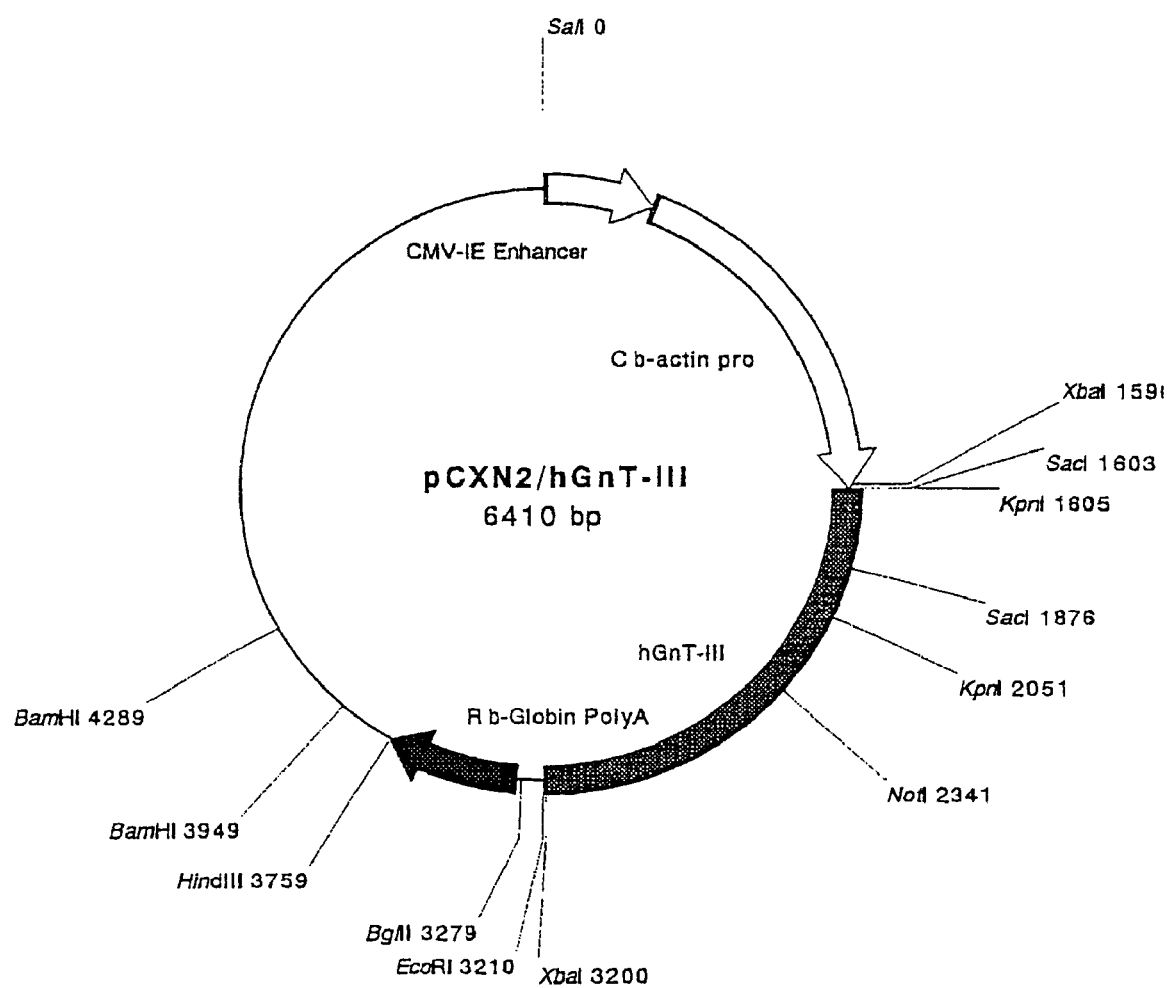
FIG. 5 illustrates the transgene structure of Example 3.

Transgenic Pigs Generated with a Transgene Comprising Cytomegalovirus Enhancer, Chicken β-actin Promoter and cDNA of GnT-III A transgene comprising the cytomegalovirus enhancer, chicken β-actin promoter (pCXN2) and cDNA of GnT-III was prepared. As shown in FIG. 5, it was identical to Example 1 except for replacing the pMCP promoter and the first intron area of DAF by pCXN2. Transgenic piglings were obtained. Thus, it was confirmed that liveborn transgenic pigs could be generated from the embryos introduced with GnT-III gene (especially, the human GnT-III gene).

Example 4

Transgenic Mice Generated with a Transgene Comprising pMCP Promoter, the First Intron of DAF and cDNA of GnT-III The transgenic mice were conventionally generated with the transgene described in Example 1.

Comparative Example 1

Transgenic Pigs Generated with a Transgene Comprising pMCP and cDNA of DAF

The transgenic pigs were generated with the transgene comprising pMCP promoter and cDNA of DAF (see Japanese Patent Publication KOKAI No. 239430/1999).

Comparative Example 2

Transgenic Mice Generated with a Transgene Comprising pMCP and cDNA of DAF

According to Comparative Example 1, transgenic mice were generated with a transgene comprising pMCP promoter and cDNA of DAF (see Japanese Patent Publication KOKAI No. 239430/1999).

Example 5

Transgenic Pigs Carrying Genes Encoding Both GnT-III and DAF

A transgenic pig (a heterozygous male) expressing GnT-III of above-described Example 3 and those (two heterozygous females) expressing DAF of above-described Comparative Example 1 were crossbred after their sexual maturation. Seventeen liveborn youngs were obtained (the total number of piglings: 18). With the youngs, the transgenes were identified by the identification methods of GnT-III and DAF described above and in Japanese Patent Publication KOKAI No.239430/1999. The piglings obtained were classified into four genotypes in a ratio of approximately 1:1:1:1; DAF(−)/GnT-III(−) (n=3), DAF(+)/GnT-III(−) (n=5), DAF(−)/GnT-III(+) (n=5) and DAF(+)/GnT-III(+) (n=4).

Such results proved that the transgenic animals simultaneously expressing GnT-III and one or more genes other than GnT-III gene (DAF in Example 5) could be generated.

Example 6

Transgenic Mice Carrying Genes Encoding Both GnT-III and DAF

The transgenic mouse (female) expressing GnT-III of above-described Example 4 and one (male) expressing DAF of above-described Comparative Example 2 were crossbred to generate the transgenic mice carrying both genes. The mice were demonstrated to carry both genes by the method described in Example 5.

Experiment 1

GnT-III Activity of the Transgenic Pig (a) Method to determine GnT-III activities: The activity of GnT-III was determined with a pyridylaminated biantennary-sugar chain as a substrate. The outline is as follows:

Various organs from transgenic pigs were homogenized in phosphate-buffered saline (PBS). After determination of the protein contents, the homogenates were incubated with UDP (uridine diphosphate)-GlcNAc as a donor substrate and 2-pyridylaminated (PA) biantennary-sugar chain as an acceptor substrate for GnT-III to produce bisecting GlcNAc, and then GnT-III activity (pmol/h/mg) was determined. Namely, the homogenates were incubated for 2 h at 37° C. in the reaction buffer consisting of 125 mM 2-(N-morpholino) ethanesulphonate, pH 6.25, containing 0.77 mM 2-aminopyridylaminated(PA) biantennary-sugar chain, 20 mM UDP-GlcNAc, 10 mM $MnCl_2$, 200 mM GlcNAc and 0.5% Triton X-100. Samples were boiled for 3 min to quench the reaction and centrifuged for 5 min at 15,000×g. The amount of GlcNAc was determined by HPLC (a Shimadzu HPLC, SCL-6A) in the following way: column; an ODS-80 column (Tosoh), elution buffer; 20 mM ammonium acetate containing 0.25% (v/v) butane-1-ol, the flow rate; 1.2 ml/min at 55° C., and detection; a fluorescence spectrophotometer (excitation and emission wavelengths 320 and 400 nm, respectively). The amount of bisecting GlcNAc was determined with 399 pmol of pyridylaminated biantennary oligosaccharide as a standard. The results of three independent experiments were averaged and the specific activity of the enzyme was expressed as pmol of transferred GlcNAc/h/mg of protein (Table 1).

(b) Results of GnT-III activity determination: The GnT-III activities of the organs of the transgenic pigs of Examples 1, 2, 3 and 5 and those of a nontransgenic normal pig are shown in Table 1.

TABLE 1

| GnT-III activities of porcine organs (pmol/h/mg) | | | | | |
|---|---|---|---|---|---|
| Organ | Example 1 | Example 2 | Example 3 | Example 5 | Normal pig |
| Brain | $148^c$ | $52^b$ | $305^d$ | $112^c$ | $0^a$ |
| Lung | $725^c$ | $324^b$ | $953^d$ | $879^{c,d}$ | $0^a$ |
| Heart | $175^c$ | $54^b$ | $435^c$ | $245^d$ | $0^a$ |
| Liver | $603^d$ | $112^b$ | $482^c$ | $450^c$ | $0^a$ |
| Kidney | $1066^d$ | $315^b$ | $1792^e$ | $1278^d$ | $0^a$ |
| Spleen | $777^d$ | $92^b$ | $607^c$ | $715^d$ | $0^a$ |
| Skin | $225^c$ | $84^b$ | $286^c$ | $254^c$ | $0^a$ |

Values bearing the different superscripts in the same row show significant differences ($p < 0.05$).

Tanemura et al. reported that the GnT-III activities of the lung and kidney of normal mice were 520 and 3,400 pmol/h/mg, resepectively (Transplant. Proc. 29: 895-896 (1997). However, no normal pig expressed GnT-III on her organs examined.

The transgenic pigs of this invention expressed GnT-III on all the organs examined. When the expression levels of GnT-III were compared among organs, the transgenic pigs with the transgene comprising pMCP promoter, the first intron of DAF and GnT-III cDNA (Example 1) expressed higher GnT-III activities in their livers and kidneys. Similarly, those with the transgene comprising cytomegalovirus enhancer, β-actin promoter and GnT-III cDNA (Examples 3 and 5) did so in their lungs, hearts, kidneys and spleens.

Because the GnT-III activities of the organs of transgenic pigs of Example 1 were higher than those of Example 2 sharing the pMCP promoter, it was confirmed that the first intron of DAF of Example 1 actedas an enhancer.

Experiment 2

The Amount of α-Gal Antigen of the Transgenic Pigs (a) Method for determining α-Gal antigens on organs of transgenic pigs (1): The amounts of α-Gal antigens on the organs were determined with IB4 lectin specifically capable of binding to the antigens. Briefly, lysate (3 μg) of the organ to be examined was electrophoresed on SDS-polyacrylaminde gel (12%) under reduced conditions. The gel was electrically transferred to a piece of nitrocellulose membrane. The membrane was blocked with 3% BSA-containing PBS, treated with biotin-conjugated IB4 lectin (10 μg/ml), washed, treated with avidin-labeled horseradish peroxidase (Vector), washed and color was developed with an ECL detection kit (Amarsham). The color intensity was determined with an image scanner. Lectin-binding ratios were obtained by averaging the results of three independent experiments and relative values were indicated to that of normal pig's organ as 100.

(b) The method for determining the α-Gal antigen and GnT-III activity in the endothelial cells of the transgenic pigs' organs (2): The transgenic pigs to be examined were sacrificed, and their aortas were excised. The endothelial cells were collected by lightly rubbing the inside of the aortas and cultured in Ham's F-12 medium with several subcultures. The amounts of the Gal antigens were determined by FACScan (Becton Dickinson) after treatment with FITC-labeled IB4 lectin.

(c) Results of α-Gal antigen determination (1): Amounts of the α-Gal antigens in the organs of the transgenic pigs of Examples 1, 3 and 5 and those of a normal, nontransgenic pig are shown in Table 2.

TABLE 2

| The amounts of α-Gal antigens on porcine organs (Relatively indicated to the amount of α-Gal antigen on normal porcine organ set as 100) | | | | |
|---|---|---|---|---|
| Organ | Example 1 | Example 3 | Example 5 | Normal pig |
| Brain | $88^a$ | $90^b$ | $90^a$ | $100^c$ |
| Lung | $30^a$ | $13^b$ | $17^b$ | $100^c$ |
| Heart | $44^a$ | $31^b$ | $32^b$ | $100^c$ |
| Liver | $20^a$ | $36^b$ | $34^b$ | $100^c$ |
| Kidney | $12^a$ | $32^b$ | $31^b$ | $100^c$ |
| Spleen | $20^a$ | $47^b$ | $45^b$ | $100^c$ |
| Skin | $80^a$ | $50^b$ | $60^b$ | $100^c$ |

The values bearing the same superscript in the same row are not significantly different ($p < 0.05$).

In the transgenic pigs of Examples 1, 3 and 5, decreased α-Gal antigen in comparison with that of the normal pig was observed. When the reduced amounts of α-Gal antigens were compared among organs, the transgenic pigs with the transgene comprising pMCP promoter, the first intron of DAF and GnT-III cDNA (Example 1) reduced the α-Gal antigens in their livers, kidneys and spleens. Similarly, those with the transgene comprising cytomegalovirus enhancer, β-actin promoter and GnT-III cDNA (Examples 3 and 5) did so in the lungs and hearts.

(d) Results of determinations of the α-Gal antigens and GnT-III activities on the endothelial cells (2): Amounts of the α-Gal antigens (expressed as FACS mean shifts) and activities of GnT-III in the endothelial cells from the transgenic pigs of Examples 3 and 5 and those of a normal, nontransgenic pig are shown in Table 3.

TABLE 3

| Alpha-Gal antigen and GnT-III activity in porcine endothelial cells | | | |
|---|---|---|---|
| | Example 3 | Example 5 | Normal pig |
| α-Gal antigen | $230^a$ | $168^a$ | $543^b$ |
| GnT-III activity | $2818^c$ | $3188^c$ | $0^d$ |

Values bearing the same superscript in the same row are not significantly different ($p < 0.05$).

It was observed that the endothelial cells of transgenic pigs of Examples 3 and 5 were expressing GnT-III, resulting in reduced α-Gal antigens.

Experiment 3

Ex Vivo Perfusion Study of the Porcine Heart (1) Determination of Prolonged Time of Cardiac Function Effects of the sugar-chain branch-reduced organs by GnT-III on hyperacute rejection were examined by the ex vivo study perfusing the human serum into the transgenic pigs' hearts. Two-week old normal and transgenic pigs of Example 1 (each n=5) were determined. The animals were anesthetized with anesthetic robonal (0.5 ml/kg) followed by sedative stresnil (2 mg/kg). Heart beating was stopped by injecting a cardioplegic solution (glucose, 0.39M; $NaHCO_3$, 8.3 mM; KCl, 80 mM, hepalin 2,000U/l) chilled to 4° C. from the abdominal aorta to the heart through a catheter. The hearts were excised and soaked in a cardioplegic solution until they were connected to a Langendorff's apparatus. After connecting the heart to the apparatus through the aorta and pulmonary vein, Krebs-Henseleit buffer (NaCl, 118.33 mM; KCl, 4.7 mM; $KH_2PO_4$, 1.2 mM; $MgCl_2$, 0.66 mM; $NaHCO_3$, 25 mM; $CaCl_2$, 0.167 mM; lactose, 11.1 mM) maintained at 35° C. was circulated. Twenty minutes later, 50% human-serum containing K-H buffer was circulated. The period of time for the heart to stop beating was recorded. The end of ventricular beating was regarded as that of the heart function. The results are shown in Table 4.

From Table 4, it was confirmed that the transgenic pig of this invention prevented the hyperacute rejection.

TABLE 4

Beating period of the porcine heart perfused ex vivo

|  | Example 1 | Normal pig |
|---|---|---|
| Period of ventricular beating (min) | 110.5 ± 29.3 | 30.5 ± 4.8 |

(2) Histological Examination After the ex vivo Perfusion

After the ex vivo perfusion, frozen sections of the pig hearts were prepared and the deposited antibody and complement were compared. Briefly a piece of the tissue was fixed with OKT compound (Miles) and frozen on dry ice/methanol immediately after the end of ex vivo perfusion. Cryostat sections of 8 µm thickness were placed on a poly-L-lysin-coated slide glass, air-dried, fixed with aceton and then treated with anti-IgG antibody (biotin-labeled anti-human IgG monoclonal antibody JDC10: Southern Biotechnology), anti-IgM antibody (biotin-labeled anti-human IgM monoclonal antibody SA-DA4: Southern Biotechnology), anti-C1q antibody (primary antibody; anti-human C1q rabbit polyclonal antibody: Cosmo Bio, secondary antibody; biotin-labeled anti-rabbit IgG monoclonal antibody D10E6: Spring Valley Laboratories) and anti-C3 antibody (primary antibody; anti-human C3 rabbit polyclonal antibody: Cosmo Bio, secondary antibody; biotin-labeled anti-rabbit IgG monoclonal antibody D10E6: Spring Valley Laboratories) after treating the endogenous biotin with a blocking kit (Vector Laboratories). Immunological staining was carried out with a Vector Laboratories' Vectastain ABC kit. The peroxidase reaction was carried out with a diaminobenzidine reagent set (Kirkegaard & Perry Laboratories). The deposits of each component was microscopically observed. The results are shown in Table 5.

TABLE 5

Immunohistological evaluation of the porcine hearts perfused ex vivo

|  | Example 1 | Normal pig |
|---|---|---|
| IgM | ++ | +++ |
| IgG | ++ | +++ |
| C1q | + | +++ |
| C3 | + | +++ |

+, ++, +++: degree of deposit of the component

From Table 5, it was confirmed that the transgenic pig of this invention prevented the hyperacute rejection. Particularly, it was confirmed that the reduced α-Gal antigens prevented the early phase (inhibition of C1q deposit) and the middle phase (inhibition of C3 deposit) of the complement reaction.

Experiment 4

Inhibition of the Complement Reaction with Erythrocytes from the Transgenic Mice Simultaneously Expressing GnT-III and DAF Offsprings individually prepared from the transgenic mice expressing GnT-III of Example 4, those expressing DAF of Example 2 and those expressing both GnT-III and DAF of Example 6 and normal mice were sacrificed. Their erythrocytes were collected and diluted with PBS. A 30-µl portion of the dilution was dispensed in a well of a 96-well microplate ($1 \times 10^7$ cells/well) and allowed to react (for 1.5 h at 37° C.) with dropwise added 70 µl of human serum, of which the complement concentration had been adjusted. Hemolysis caused by the complement reaction was determined by reading the optical densities at 405 nm and expressed relatively to that of normal mouse set at 100. The results are shown in Table 6.

TABLE 6

Complement-dependent haemolysis of the erythrocytes of the mice (relative to haemolysis of normal mouse set at 100)

| Concentration of normal human serum | Example 4 | Comparative Example 2 | Example 6 |
|---|---|---|---|
| 20% | 78.6 | 35.7 | 8.6 |
| 50% | 87.0 | 44.2 | 10.4 |

From Table 6, it was confirmed that the transgenic mice of this invention prevented complement-dependent cytotoxicity (complement reaction). It was also confirmed that simultaneous expression of both GnT-III and DAF synergistically prevented the complement-dependent cytotoxicity. Furthermore, it was confirmed that the expression of sugar-chain-modifying enzyme GnT-III did not injure the expression of GPI-anchored sugar protein DAF.

Experiment 5

Inhibition of the Complement Reaction with the Erythrocytes from the Transgenic Pig Simultaneously Expressing GnT-III and DAF (a) The method of complement-reaction inhibition assay: The complement-dependent cytoxicity was determined by allowing to react the porcine endothelial cells and the human serum. Transgenic pigs of Examples 1, 3 and 5 and a normal pig were sacrificed and their aortas excised. Endothelial cells were collected by lightly rubbing the inside of the aortas, cultivated in F-12 medium, and subcultured 5-10 times in DMEM. Thereafter, they were dispensed in wells of a 96-well microplate ($5 \times 10^3$ cells/well), incubated overnight, washed with PBS(−) and allowed to react (for 1.5 h at 37° C.) with dropwise-added 100 µl of either non-inactivated or complement concentration-adjusted human serum (30% and 50%). The surviving cells were counted with lactate dehydrogenase as an indicator. The survival ratio was calculated by the following equation: survival ratio (%)=(number of surviving cells after the complement reaction with complement concentration-adjusted human serum)/(that with non-inactivated human serum)×100. The results are shown in Table 7.

TABLE 7

Survival ratios of porcine endothelial cells undergone the complement reaction

| Ratio of normal human serum | Example 1 | Example 3 | Example 5 | Normal pig |
|---|---|---|---|---|
| 30% | 27.7[a] | 43.3[b] | 67.6[c] | 14.8[d] |
| 50% | 19.4[e] | 39.8[b] | 66.3[c] | 5.4[f] |

The values bearing distinct superscripts in the same row are significantly different ($p < 0.05$).

(b) Tests for prevention of the cytotoxicity: From Table 7, it was confirmed that the transgenic pig of this invention prevented the complement-dependent cytotoxicity (complement reaction). It was also confirmed that the simultaneous expression of both GnT-III and DAF synergistically prevented the complement-dependent cytotoxicity. Furthermore, it was confirmed that the expression of the sugar-chain modifying enzyme GnT-III did not injure the expression of GPI-anchored sugar protein DAF.

Experiment 6

Inhibition of NK Cell-dependent Cytotoxicity by the Endothelial Cells from the Transgenic Pig Simultaneously Expressing GnT-III and DAF According to Experiment 5, the endothelial cells were prepared from the transgenic pigs of Examples 3 and 5 and normal pigs, dispensed in wells of a 96-well microplate ($2\times10^4$ cells/well), which were incubated overnight, washed with PBS(−) and allowed to react (for 4 h at 37° C.) with a dropwise-added 50 µl of NK cell suspension ($4\times10^6$ cells/ml) separated from human blood. The surviving cells were counted with lactate dehydrogenase as an indicator. The survival ratio was calculated by the following equation: survival ratio (%)=(number of surviving cells after the reaction with NK cells)/(that without NK cells)×100. The results are shown in Table 8.

TABLE 8

Survival ratios of porcine endothelial cells after reaction with NK cells

| Example 3 | Example 5 | Normal pig |
|---|---|---|
| 57.9[a] | 62.1[a] | 44.2[b] |

Values bearing distinct superscripts are significantly different ($p < 0.05$).

From Table 8, it was confirmed that the transgenic pig expressing GnT-III of this invention prevented the NK cell-dependent cytotoxicity. Although precise factors implicated in the initiation of AVR have not necessarily been identified, xenoreactive antigens, complement, macrophages, NK cells, neutrophils, and platelets are considered to be involved. Because the endothelial cells of the transgenic pig of this invention are resistant to NK cell-dependent cytotoxicity and possessing reduced xenoreactive antigens (α-Gal antigens) as Experiment 2 shows, the transgenic pig of this invention may be resistant to acute vascular rejection.

We claim:

1. A transgenic pig, whose genome comprises a transgene encoding human N-acetylglucosaminyltransferase (GnT III), for providing organs for xenotransplantation comprising:
   regulatory sequences capable of functioning in the hyperacute rejection-occurring local cells, wherein said regulatory sequences are:
   (A) a promoter of porcine complement inhibitor and the first intron of a human CD55 gene, or
   (B) a cytomegalovirus (CMV) enhancer and chicken beta-actin promoter, and
   said transgene encoding human N-acetylglucosaminyltransferase III (GnT III),
   wherein said regulatory sequences are operably linked to said transgene encoding human GnT III, and
   wherein said transgenic pig expresses GnT III in one or more organs selected from the group consisting of: heart, liver, lung, kidney and spleen, and
   wherein expression of GnT III decreases expression of galactose-α-1,3-galactose antigen in the one or more organs selected from the group consisting of: heart, liver, lung, kidney and spleen, thereby decreasing hyperacute rejection in a human after xenotransplantation of said one or more organs into a human.

2. A method of producing a transgenic pig according to claim 1, which comprises:
   introducing said transgene encoding human GnT III into a pig pronuclei of a pre-nuclear phase pig egg by microinjection to produce a transgenic pig
   wherein said transgene encoding GnT III is operably linked to:
   (A) a promoter of porcine complement inhibitor and the first intron of a human CD55 gene, or
   (B) a cytomegalovirus (CMV) enhancer and chicken beta-actin promoter,
   thereby producing a transgenic pig whose genome comprises the transgene encoding human GnT III.

3. A transgenic pig, whose genome comprises a first transgene encoding human N-acetylglucosaminyltransferase III (GnT III) and whose genome comprises a second transgene encoding human complement inhibitor CD55, for providing organs for xenotransplantation comprising:
   said first transgene encoding human N-acetylglucosaminyltransferase III (GnT III) operably linked to a cytomegalovirus (CMV) enhancer and a chicken beta-actin promoter, and
   said second transgene encoding human complement inhibitor CD55 operably linked to a promoter of porcine complement inhibitor,
   wherein said transgenic pig expresses GnT III in one or more organs selected from the group consisting of: heart, liver, lung, kidney and spleen, and
   wherein expression of GnT III decreases expression of galactose-α-1,3-galactose antigen in the one or more organs selected from the group consisting of: heart, liver, lung, kidney and spleen, thereby decreasing hyperacute rejection in a human after xenotransplantation of said one or more organs into a human.

4. A method of producing a transgenic pig according to claim 3, which comprises:
   producing separately a first transgenic pig expressing human GnT III and a second transgenic pig expressing the human complement inhibitor CD55 by introducing said first transgene encoding human GnT III into a pig pronuclei of a first pre-nuclear phase pig egg by microinjection to produce a first transgenic pig, and introducing said second transgene encoding human complement inhibitor CD55 into a pig pronuclei of a second pre-nuclear phase pig egg by microinjection to produce a second transgenic pig, and
   breeding the first and second transgenic pigs to produce transgenic offspring,
   wherein said transgenic offspring express both human GnT III and human complement inhibitor CD55, and
   wherein said first transgene encoding GnT III is operably linked to a cytomegalovirus (CMV) enhancer and chicken beta-actin promoter, and
   wherein said second transgene encoding a human complement inhibitor CD55 is operably linked to a promoter of porcine complement inhibitor.

* * * * *